(12) United States Patent
Abu Hassan et al.

(10) Patent No.: US 7,932,409 B2
(45) Date of Patent: Apr. 26, 2011

(54) PROCESS TO PRODUCE POLYOLS

(75) Inventors: Hazimah Abu Hassan, Selangor (MY); Tuan Noor Maznee Tuan Ismail, Selangor (MY); Mohd Norhisham Sattar, Selangor (MY); Seng Soi Hoong, Kuala Lumpur (MY); Tian Lye Ooi, Selangor (MY); Salmiah Ahmad, Selangor (MY); Kosheela Devi a/p Poo Palam, Selangor (MY); Mei Yee Cheong, Selangor (MY)

(73) Assignee: Malaysian Palm Oil Board, Selangor (MY)

( * ) Notice: Subject to any disclaimer, the term of this patent is extended or adjusted under 35 U.S.C. 154(b) by 424 days.

(21) Appl. No.: 12/057,444

(22) Filed: Mar. 28, 2008

(65) Prior Publication Data
US 2008/0293913 A1    Nov. 27, 2008

(30) Foreign Application Priority Data

May 22, 2007 (MY) ............................... PI 2007 0797

(51) Int. Cl.
  *C07D 301/32* (2006.01)
  *C08G 65/02* (2006.01)
(52) U.S. Cl. ........ 549/541; 549/513; 549/525; 549/526; 549/527; 528/361; 528/271
(58) Field of Classification Search ................. None
  See application file for complete search history.

(56) References Cited

U.S. PATENT DOCUMENTS

| | | | |
|---|---|---|---|
| 2,903,465 A * | 9/1959 | Suter et al. | 549/527 |
| 2,948,669 A * | 8/1960 | Remes | 208/7 |
| 3,328,430 A * | 6/1967 | Hansen et al. | 549/527 |
| 3,827,993 A * | 8/1974 | Cunningham | 530/233 |
| 4,423,239 A * | 12/1983 | Miyazaki et al. | 549/541 |
| 4,508,853 A * | 4/1985 | Kluth et al. | 521/107 |
| 5,262,496 A * | 11/1993 | Bening et al. | 524/507 |
| 6,107,433 A * | 8/2000 | Petrovic et al. | 528/1 |
| 6,433,121 B1 | 8/2002 | Petrovic et al. | |
| 6,548,609 B2 | 4/2003 | Ramirez-de-Arellano-Aburto et al. | |
| 6,734,315 B1 | 5/2004 | Nowak et al. | |
| 2007/0037953 A1 | 2/2007 | Geiger et al. | |

FOREIGN PATENT DOCUMENTS

MX   PA04002965   7/2004

OTHER PUBLICATIONS

Gou, A. et al., Vebetable Oils-Based Polyols, 2005, Industrial Uses of Vegetable oil, Sevim Z. Erhan, Chapter 6, 22 pages.*

* cited by examiner

*Primary Examiner* — Jafar Parsa
*Assistant Examiner* — Yate K Cutliff
(74) *Attorney, Agent, or Firm* — Preston Smirman; Smirman IP Law, PLLC

(57) ABSTRACT

A process for producing oleochemical polyols comprises the steps of epoxidizing unsaturated oil using an organic acid together with oxygenated water or a per-acid to obtain epoxidized oil; washing the epoxidized oil with salt water to remove unused organic acid together with oxygenated water or a per-acid; neutralizing acidic condition of the washed epoxidized oil with a base; washing the neutralized epoxidized oil with a salt solution until the pH of the neutralized epoxidized oil reaching 6.5 to 7.5 to removed the base residue; drying the washed neutralized epoxidized oil under vacuum; and reacting the washed neutralized dried epoxidized oil with polyhydric alcohol in the presence of boron trifluoride-diethylether complex to produce the oleochemical polyols. The oleochemical polyols are then subjected to the same washing, neutralizing, washing and drying process as in preparing the washed neutralized dried epoxidized oil.

16 Claims, 1 Drawing Sheet

PROCESS TO PRODUCE POLYOLS

RELATED APPLICATIONS

Figure 1:
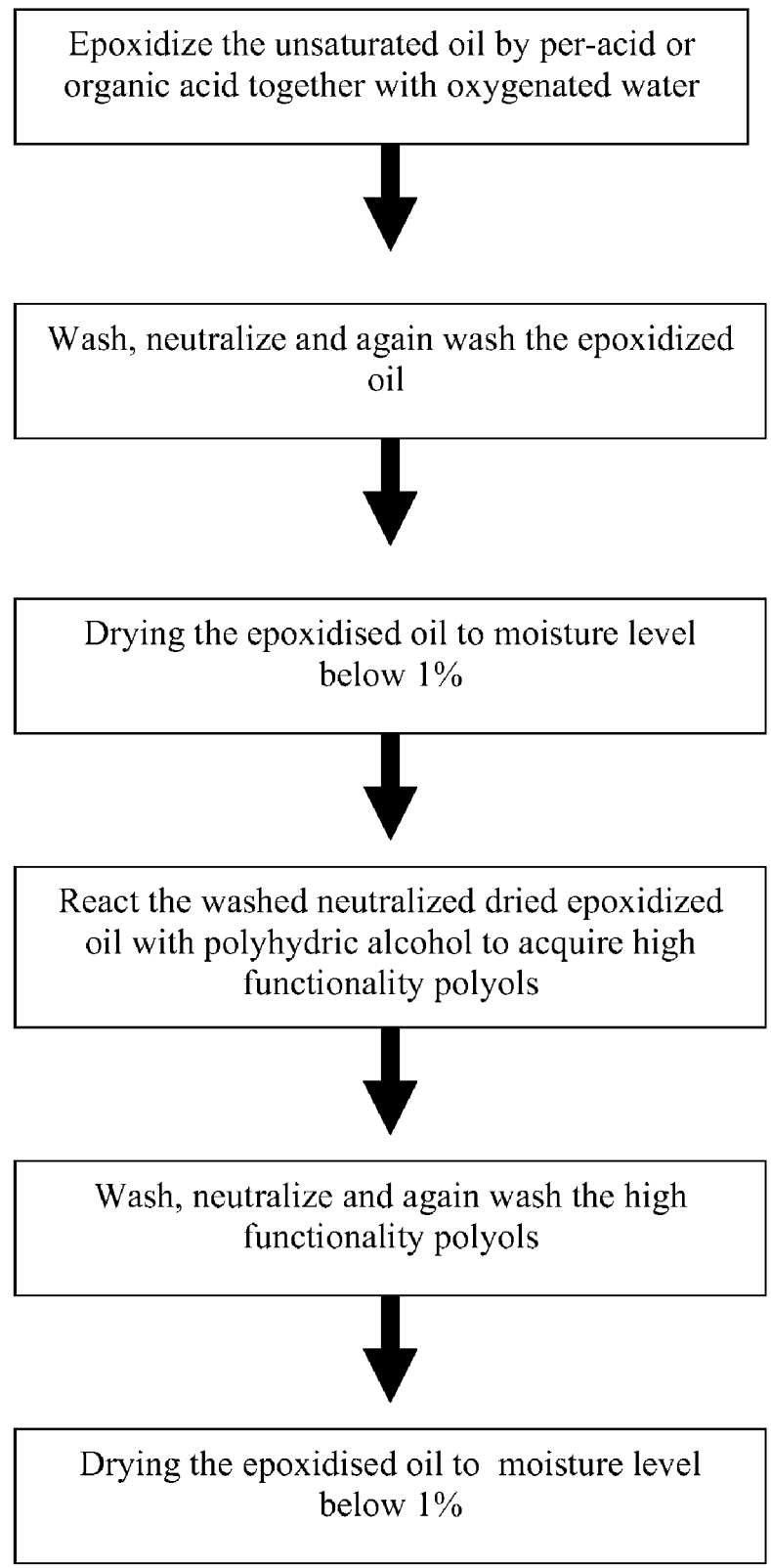

The present application is based on, and claims priority from, Malaysian Application Number PI 2007 0797, filed May 22, 2007, the disclosure of which is hereby incorporated by reference herein in its entirety.

FIELD OF THE INVENTION

The present invention relates to a process encompassing purification step of intermediate product during the process of producing polyols from unsaturated oil and fat which preferably derives from renewable resource, thus rendering the produced polyols possess the desired properties to be used for different applications.

BACKGROUND OF THE INVENTION

Most of the polyols that are used in polyurethane industries originated from petroleum-based chemicals, which can be categorized into two classes (a) hydroxyl-terminated polyethers and (b) hydroxyl-terminated polyesters. The polyether polyols of most interest in polyurethane industries are polypropylene glycols and polytetramethylene glycols, in which their manufacture involves the addition polymerization of the monomeric epoxide. On the other hand, the polyesters are prepared by reaction of dibasic acids with diol or alcohols with higher functionality alcohol.

However, as the world's petroleum resources are depleting coupled with its ever-increasing prices, polyurethane producers worldwide have been looking into renewable/sustainable raw materials to replace petroleum-based polyols. An ideal alternative feed stock will be natural oils and fats, which can derive from both plants and animals sources. Plenty of patent applications have been filed regarding different approaches in producing the polyols from the natural source in order to provide a solution to effectively produce polyols with the desired qualities. Nonetheless, polyols produced by the prior arts are vary in terms of quality as the intermediate product being employed for producing the polyols are not subjected to prior purification.

Nicolás et al. disclosed a patent application in U.S. Pat. No. 6,548,609 regarding a process for obtaining oleochemical polyols from natural oils and/or fats. The disclosed process utilizes a planar Lewis acid for the alcoholysis process and large amount of energy has to be provided during the alcoholysis as the reaction temperature is above 200° C. Due to the drastic condition applied and no purification on the epoxidized oil, the yield of the desired products via the disclosed process is very low as most of the substrates are converted to side products.

U.S. Pat. No. 6,433,121 is another patent disclosed a process to produce vegetable oil-based polyols which can be subsequently used for polyurethane production. In the disclosed process, fluoroboric acid is employed as the catalysts to improve the alcoholysis or hydrolysis of the epoxidized oil. Besides alcohol, water also being used as a reactant to hydrolyze the epoxidized oil. The process disclosed does not include purification or neutralizing step for the epxoidized oil, it is known that acidic condition renders the epoxidized compounds vulnerable to attack from nucleophile such as water. Thus, the process disclosed in this application is unlikely to be used for synthesis long chain polyols or high functionality polyols via reaction between the epoxidized oil with other polyhydric alcohol as most of the epoxidized oil reacts with water molecule first rather than the polyhydric alcohol.

U.S. Pat. No. 6,734,315 filed a process to expoxidize unsaturated compounds using a thin film reactor and no catalyst employed during the epoxidation process. On the other hand, patent MXPA04002965 claims an epoxidation process by using clay as the catalysts to accelerate the alcoholysis process between alcohol compounds and epoxidized oil. Geiger et al. filed an application under US patent no. 2007037953 to claim an epoxidation process using organometallic catalysts instead of conventional organic oxidation reagents such as per-acids. All the above mentioned prior arts have shown no attempt in purifying and/or neutralizing the acidic condition of the epoxidized oil before subjecting the epoxidized oil for alcoholysis to produce high functionality polyols. Therefore, the polyols produced can be varied in terms of quality. Nevertheless, the polyols shall be purified too before incorporated with other chemical compounds in manufacturing polyurethane as the remaining chemical residues are normally capable of initiating polymerization of the monomers which maybe not desired in production of polyurethane.

SUMMARY OF THE INVENTION

The present invention aims to disclose a process utilizing sustainable resources in production of polyols for different applications.

Another object of the present invention is to disclose a novel catalyst in enhancing the alcoholysis reaction in producing polyols from epoxidized oil.

Still another object of the present invention is to provide a solution in controlling quality and property of the produced polyols via epoxidation and alcoholysis of the unsaturated oil by purifying and stabilizing the intermediate products of the process.

Further object of the present invention includes providing steps to purify the polyols produced from the natural oil and/or fat thus ensuring further reaction incorporating the polyols for different application is not affected by the chemical residues derive from previous reaction.

At least one of the preceding objects is met, in whole or in part, by the present invention, in which one of the embodiments of the present invention involves a process for producing oleochemical polyols comprises the steps of epoxidizing unsaturated oil using an organic acid together with oxygenated water or a per-acid to obtain epoxidized oil; washing the epoxidized oil with salt water to remove unused organic acid together with oxygenated water or the per-acid; neutralizing acidic condition of the washed epoxidized oil with a base; washing the neutralized epoxidized oil with a salt solution until the pH of the neutralized epoxidized oil is 6.5 to 7.5 to removed the base residue; and reacting the washed neutralized epoxidized oil with polyhydric alcohosl in the presence of boron trifluoride-diethylether complex to produce the oleochemical polyols.

Another embodiment of the disclosed process further comprises the step of drying the washed neutralized epoxidized oil before the epoxidized oil reacts with polyhydric alcohol.

Still another embodiment of the disclosed process includes the purifying steps of washing the produced oleochemical polyols with salt water; neutralizing acidic condition of the wash oleochemical polyols with a base; and washing the neutralized oleochemical polyols with the salt water until the pH of the neutralized oleochemical polyols reaching 6.5 to 7.5 to remove the base residue.

In the preferred embodiment of the present invention, unsaturated oil employed in the disclosed process is any one or combination of palm oil, soybean oil, coconut oil, groundnut oil, safflower oil, linseed oil, corn oil, sunflower oil, olive oil, canola oil, cottonseed oil, rapeseed oil, tung oil, fish oil, lard, tallow and any derivatives thereof.

On the other hand, the oxidizing agent to epoxidize the unsaturated oil is preferably per-acid selected from the group consisting of peroxyformic acid, peroxyacetic acid, trifluoroperoxyacetic acid, benzyloxyperoxyformic acid, 3,5-dinitroperoxybenzoic acid, and, -chloroperoxybenzoic acid.

In respect to one of the embodiments, the base employed in the disclosed process to neutralize the acidic condition in both epoxidized oil and produced polyols can be ammonia, metal carbonates, metal bicarbonates or anionic ion-exchange resin.

In further embodiment of the present invention, the polyhydric alcohol utilized is any one or combination of glycerol, pentaerythritol, ethylene glycol, propylene glycol, trimethylolpropane, sorbitol, xylitol, sucrose, D-glucose and fructose.

Still other objects and advantages of the present invention will become readily apparent to those skilled in the art from the following detailed description, wherein the preferred embodiments of the invention are shown and described, simply by way of illustration of the best mode contemplated of carrying out the invention. As will be realized, the invention is capable of other and different embodiments, and its several details are capable of modifications in various obvious aspects, all without departing from the invention. Accordingly, the drawings and description thereof are to be regarded as illustrative in nature, and not as restrictive.

BREIF DESCRIPTION OF THE DRAWING

The present invention is illustrated by way of example, and not by limitation, in the figures of the accompanying drawings, wherein elements having the same reference numeral designations represent like elements throughout and wherein:

FIG. 1 shows the flow of the disclosed process in producing polyols.

DETAILED DESCRIPTION OF THE INVENTION

One skilled in the art will readily appreciate that the present invention is well adapted to carry out the objects and obtain the ends and advantages mentioned, as well as those inherent therein. The embodiment describes herein is not intended as limitations on the scope of the invention.

The term "unsaturated oil" used throughout the specification herein refers to both unsaturated oil and unsaturated fat derive from naturals source like animals and plants.

The term "washing" used throughout the specification herein refers to the action where the washing solvent, salt water in present invention, is brought into contact to the produced oleochemcial by means of vortex, stirring or agitation to remove the unwanted compounds.

The present invention relates to a process for producing oleochemical polyols comprises the steps of epoxidizing unsaturated oil using an organic acid together with oxygenated water or a per-acid to obtain epoxidized oil; washing the epoxidized oil with salt water to remove unused organic acid together with oxygenated water or the per-acid; neutralizing acidic condition of the washed epoxidized oil with a base; washing the neutralized epoxidized oil with the salt water until the pH of the neutralized epoxidized oil reaching 6.5 to 7.5 to removed the base residue; reacting the washed neutralized epoxidized oil with polyhydric alcohols in the presence of boron trifluoride-diethylether complex to produce the oleochemical polyols.

It is important to be noted that no catalyst is employed in the preferred embodiment of the disclosed process for epoxidation of the unsaturated oil, but one skilled in the art shall know that incorporation of a suitable catalyst such as concentrated sulfuric acid is feasible in the epoxidation process thus any modification thereof shall not depart from the scope of the present invention. In the preferable embodiment, the epoxidation process is performed at 35° C. to 65° C. Possibly, the epoxidation can be performed at higher temperature though the per-acid may be ignited or the unsaturated oil may be over-oxidized to other side-product instead of the desired epoxidized oil.

Any unsaturated oil can be employed in the disclosed process for producing the polyols. For example, but not limited to, palm oil, soybean oil, coconut oil, groundnut oil, safflower oil, linseed oil, corn oil, sunflower oil, olive oil, canola oil, cottonseed oil, rapeseed oil, tung oil, fish oil, lard, tallow and any derivatives thereof. The oil derivatives mentioned herein can be processed oil product such as palm olein or palm kernel olein. Moreover, it is possible to mix plurality types of unsaturated oil to produce polyols possessing the desired properties such as low viscosity or high functionality which can be applied then for different applications.

Attention is now turned to the oxidizing agent used in the present invention to epoxidized the unsaturated oil. Any per-acid or peroxyacids or combination of peroxyacids can be employed in the present invention to epoxidized the unsaturated oil. Representative examples, but not limited to, are peroxyformic acid, peroxyacetic acid, trifluoroperoxyacetic acid, benzyloxyperoxyformic acid, 3,5-dinitroperoxybenzoic acid, and m,-chloroperoxybenzoic acid. In the most preferable embodiment, peroxyformic acid or peroxyacetic acid is used as the oxidizing agent. The peroxyacids can be pre-formed before reacting with the unsaturated oil or prepared in-situ in the reactor where the epoxidation process being carried out. No matter the peroxyacid is pre-formed or produced in-situ, the epoxidation has to be closely controlled within the favored reaction rate which can be achieved by adjusting the rate of adding or forming the peroxyacid in the unsaturated oil. Preferably, the molar ratio of peroxyacid to mole of unsaturated bond in the unsaturated oil is 0.1 to 3:1. Most preferably the molar ratio of peroxyacid to mole of unsaturated bond in the unsaturated oil is 0.5 to 1:1

Under the condition which the peroxyacid required to be pre-formed, the peroxidation of the organic acid can only achieved by high molar ratio of organic acid to hydrogen peroxide. Precaution has to be taken when preparing the pre-formed peroxyacid as too high concentration of peroxyacid in the organic acid may lead to explosion. Preferably, the molar ratio of organic acid to hydrogen peroxide in the pre-formed peroxyacid process is 3:1-2.

On the other hand, peroxyacid formed in-situ is a safer route to perform the epoxidation. In the preferred embodiment, the organic acid is pre-mixed with the unsaturated oil and the hydrogen peroxide dissolved in water is introduced into the mixture to form the peroxyacid that in turn epoxidize the unsaturated oil. Preferably, the molar ratio of organic acid to hydrogen peroxide in the peroxyacid formed in-situ process is 1:1 to 5. Most preferably the molar ratio of organic acid to hydrogen peroxide in the peroxyacid formed in-situ process is 1:1.5 to 2.5. The shortcoming of this approach is that only small amount of peroxyacid can be formed per batch and peroxyacid depletes quickly in the reaction. Formic acid or acetic acid is employed in the preferred embodiment to produce the peroxyacid in-situ. Lewis acid may be added as catalysts to improve the reaction between organic acids and hydrogen peroxide in the production of peroxyacids.

After the epoxidation reaction, the resultant products consist of an aqueous layer and an epoxidized oil layer. The epoxidation reaction is considered complete when the oxirane oxygen content of the epoxidized oil is at least about 60% of the theoretical oxirane oxygen content. The aqueous layer mainly constitute of water, organic acid and some peroxide. Whereas, the epoxidized oil layer contains some organic acid and residual peroxide that must be removed or neutralized as these residue shall significantly affect the yield of the subsequent alcoholysis. According to the preferred embodiment of the present invention, the aqueous layer can be easily drained off from the reactor by any known method. Then, the epoxidized oil layer is subjected to washing by salt water. It is known in the art that epoxidized oil layer can be washed simply by water to get rid of the organic acids and hydrogen peroxide, but always the washed epoxidized oil ends up in emulsion form. However, in the present invention, the salt content in the water has greatly reduced the surface tension of the water. Hence, emulsion will not form after the washing step using salt water. It is found by the inventor of the present invention that the salt water used shall possess a concentration of 4% to 30% in order to avoid emulsion forming in the washing step.

Likewise, the salt water with the chemical residues is drained off after the washing step. Immediately, a base, preferably in solution form, is added into the washed epoxidized oil to neutralize the acidic condition. In more specific, the base reacts with the remaining acids or hydrogen peroxide in the epoxidized oil. All the acids are considered totally neutralized when the pH of the epoxidized oil reaching basic mildly, preferably pH of 7.5 to 9. In respect to the preferred embodiment of the present invention, base employed in the disclosed process is preferably weak base to prevent drastic shift in pH during the neutralizing step. Nonetheless, strong base can be used also in the present invention. The base is preferably selected from the group consisting of ammonia, metal carbonates, metal bicarbonates and anionic ion-exchange resin. The concentration of the base prepared in solution can range from, but not limited to, 1% to 20%. In the most preferred embodiment, sodium carbonate or sodium hydrogen carbonate is used in the present invention. In order to remove the unused base in the epoxidized oil, the epoxidized oil again is washed by the salt water until the pH becomes about neutral, preferably 6.5 to 7.5. Then, the salt water is drained off. Then the washed neutralized epoxidized oil is dried until the moisture level below 5%, preferably, is below 1% before alcoholysis.

In the most preferred embodiment of the present invention, the alcoholysis is conducted in the presence of boron trifluoride-diethylether complex as the catalyst. During the alcoholysis, alcohols used in the reaction will substitute the diethyl ether in the catalyst (boron trifluoride diethyl ether complex) and form a complex with boron trifluoride. The formation of polyhydric alcohol-boron trifluoride complex would enable the insertion of polyhydric alcohol onto the epoxide ring during alcoholysis. It is well known in the art that higher the catalyst concentration tends to cause undesired side reaction such as transesterification and cross-linkage giving products of higher viscosity and lower functionality group. It was found in the present invention that the boron trifluoride-diethylether complex used in the alcoholysis preferably ranges from 0.1% to 10% of the total weight of the reactant. Another important factor to determine the extent of the side product produced is the temperature where the alcoholysis is conducted. Similar to catalyst concentration, higher temperature may accelerate the alcoholysis reaction but tend to cause undesired reaction such as transesterification at the same time. Therefore, the temperature of the alcoholysis is preferably maintained within a temperature of 60° C. to 100° C. to diminish the side reactions yet provide high yield of the desired products.

During the alcoholysis, the epoxide ring of the epoxidized oil will be opened due to neucleophilic addition of the polyhydric alcohols used under the influence of catalyst. In the most preferred embodiment, the catalyst is first pre-mixed with the polyhydric alcohol only then being charged into the epoxidized oil to initiate the alcoholysis reaction. Still, the disclosed process can progress smoothly without the pre-mixing of the polyhydric alcohol and the catalysts as long as the catalyst is presented during the reaction. The amount of the polyhydric alcohol used relies upon the amount and type of epoxidized oil, preferably not less than the mole of oxirane oxygen retained in the epoxidized oil. Polyhydric alcohol in excess amount can be employed to prevent polymerization during the alcoholysis reaction. Examples of polyhydric alcohol may be used in the disclosed process include, but are not limited to, any one or combination of glycerol, pentaeythritol, ethylene glycol, propylene glycol, trimethylolpropane, sorbitol, xylitol, sucrose, D-glucose and fructose. The alcoholysis reaction is considered complete when the oxirane oxygen content of the reactant reaches 0.5% or below.

Optionally, the disclosed process of the present invention may include purifying steps to clean the chemical residue in the produced polyols after the alcoholysis reaction. It is important to be noted that the boron trifluoride in the complex used as catalysts may react with the hydroxyl groups in the alcohol provided to form acidic compounds such as boric acid and fluoroboric acid. Therefore, removal of these acidic residues is necessary in improving stability of the produced end products as well as it shelf life. The purifying steps include washing the produced oleochemical polyols with salt water; neutralizing acidic condition of the wash oleochemical polyols with a base; and washing the neutralized oleochemical polyols with salt water until the pH of the neutralized oleochemical polyols reaching 6.5 to 7.5 to remove the base residue. The reasons of using salt water and the base are same as foregoing description. Likewise the concentration of the salt is preferably 4% to 30% and the concentration of the base is preferably 1% to 20%. Both representative examples of salt types and base are similar to the examples given in the set forth description. Further embodiment involves drying step like vacuum drying to remove the remaining water content in the polyols.

Besides, another embodiment of the present invention may include a process to purify epoxidized oil produced from a reaction between per-acid and unsaturated oil comprises the steps of washing the epoxidized oil with salt water; neutralizing acids in the washed epoxidized oil with a base; and removing the weak base by washing the neutralized epoxidized oil with salt water until the pH of the neutralized epoxidized oil is 6.5 to 7.5 to acquire the purified epoxidized oil. It is known in the art that chemical residues remained in the epoxidized oil shall directly affect the subsequent process which utilizing the epoxidized oil. Thus, the epoxidized oil shall be cleaned or purified before proceeding to the subsequent reactions. The disclosed purifying process can be adapted into other similar process as shown in the foregoing description of another embodiment of the present invention. The per-acid mentioned can be any one or combination of peroxyformic acid, peroxyacetic acid, trifluoroperoxyacetic acid, benzyloxyperoxyformic acid, 3,5-dinitroperoxybenzoic acid, and ,-chloroperoxybenzoic acid. On the other hand, the unsaturated oil is any one or combination of palm oil, soybean oil, coconut oil, groundnut oil, safflower oil, linseed oil, corn oil, sunflower oil, olive oil, canola oil, cottonseed oil, rapeseed oil, tung oil, fish oil, lard, tallow and any derivatives thereof. Moreover, the type of salts used shall not pose interference on the properties of the epoxidized oil or the subsequent reaction. Preferably the salt type is any one or combination of potassium chloride, sodium chloride and lithium chloride. Meanwhile the weak base is selected from the group consisting of ammonia, metal carbonates, metal bicarbonates and anionic ion-exchange resin. The purifying process further comprises a drying step to remove the remaining water content to below 5%, preferably, to below 1% level. Meanwhile, the remaining diethyl ether would be evaporated as gas by the drying step without leaving any trace residues in the produced polyols. Nevertheless, portion of the diethyl ether is evaporated as gas also under the influence of the high temperature along the process of the alcoholysis.

The following example is intended to further illustrate the invention, without any intent for the invention to be limited to the specific embodiments described therein.

EXAMPLE 1

Refined, bleached and deodorized (RBD) palm kernel olein (2700 g) was charged into 10 L reaction vessel and soya bean oil (SBO) (300 g) was charged into the same vessel. The ratio between RBD palm kernel olein and SBO in the oil mixture is 9 to 1 respectively. In another vessel, the required amount of hydrogen peroxide (50%, 731.34 g) and formic acid (94%, 197.89 g) for the epoxidation reaction was mixed and kept cool at temperature of 15° C. throughout the reaction. While the oil blend was stirred, the mixture of hydrogen peroxide and formic acid was slowly added into the oils blend (drop-wise). The epoxidation was conducted at temperature 40° C.-60° C. for about 2 to 3 hours. The epoxidation reaction was completed when the oxirane oxygen content (OOC) of the oil blend reached about 2.02%, which is about 89% of the theoretical OOC value. Then, the epoxidized oil were separated from the spent acids and washed with 4% NaCl solution (twice), followed by 1% sodium carbonate until the pH of the aqueous reached 8 to 9. Following that, the epoxidized oil were washed again with 4% NaCl solution in order to remove the residual sodium carbonate solution, until the aqueous layer was neutralized. After that, the neutralized epoxidized oil mixture was dried under vacuum. The yield of the epoxidized oils blend is about 89%. The moisture content in the oil after drying was 0.05% and the oxirane oxygen content was 2.02%.

EXAMPLE 2

The dried and neutralized epoxidized oils blend (2745 g) from example 1, with oxirane oxygen content of 2.02% and moisture content of 0.05% was charged into a 10 L reactor flask and then heated up to 60° C. The required amount of ethylene glycol needed for epoxy ring-opening reaction (alcoholysis) was about 193 g, based on the oxirane oxygen content of the epoxidized oils. The amount of ethylene glycol weighed was mixed with 12.15 ml of boron trifluoride ($BF_3$) (48% in diethyl ether) to form a complex. When the temperature of the epoxidized oils mixture reached 60° C., the prepared complex of ethylene glycol and boron trifluoride was charged in portions into the same reactor. During the reaction, the oxirane oxygen content decreases from the initial value of 2.02% to about 0.01%, indicating the ring opening with ethylene glycol. The product was washed with 4% NaCl solution followed by 1% sodium carbonate solution until the pH of the aqueous solution about pH 8 to 9. Then it was washed again with 4% NaCl solution to remove the residual carbonate solution. The neutralized polyol product was dried under vaccum at 80° C. to give the desired polyols of about 90-95% yield.

Properties of the polyol can be summarized as following:
a) OHV: 70-90 mg KOH per gram sample,
b) AV: 0.3-1.0 mg KOH per gram sample,
c) IV: 5-15 g $I_2$ per 100 g sample,
d) moisture content: less than 0.05%,
e) OOC: 0.01%
f) viscosity: 600 to 800 cP at 25° C.

EXAMPLE 3

The procedure in example 1 was repeated using the blend 80:20 in which 2400 g of RBD palm kernel olein was blended with 600 g of SBO in a 10 liters vessel. For the epoxidation reaction, the required amount of hydrogen peroxide (50%) was 940 g and formic acid (94%) was 254.4 g. The product was worked-up in the usual manner described in example 1. The yield of the epoxidized oil obtained was about 88%. The moisture content after drying: 0.04% and OOC: 2.6%.

EXAMPLE 4

About 2810 g of the dried epoxidized oils from example 3 was subjected to alcoholysis reaction with ethylene glycol and boron trifluoride complex as described in Example 2. The required amount of ethylene glycol and boron trifluoride are 280.93 g and 12.43 ml respectively. The product was worked-up in the manner described in example 2 to give the yield of the desired product about 90-95%.

Properties of the polyol can be summarized as following:
a) OHV: 80-100 mg KOH per gram sample,
b) AV: 0.3-1.0 mg KOH per gram sample,
c) IV: 5-15 g $I_2$ per 100 g sample,
d) moisture content: 0.04%,
e) OOC: 0.01%,
f) viscosity: 3200-3800 cP at 25° C.

EXAMPLE 5

The procedure in example 1 was repeated using a blend of RBD palm olein and RBD palm kernel olein (9:1) where 2700 g of RBD palm olein was blended with 300 g of RBD palm kernel olein in a 10 liters vessel. For the epoxidation reaction, the required amount of hydrogen peroxide (50%) was 288 g and formic acid (94%) was 1064.4 g. The product was worked-up in the usual manner described in example 1. The yield of the epoxidized oil obtained about 88%. The moisture content after drying is 0.062% and OOC is 3.017%.

EXAMPLE 6

3000 g of the dried epoxidized oils from example 5 was subjected to alcoholysis reaction with ethylene glycol and boron trifluoride complex as described in example 2. The required amount of ethylene glycol and boron trifluoride are 348.75 g and 7.96 ml respectively. The product was worked-up in the manner described in example 2 to give the yield of desired product about 90-95%.

Properties of the polyol can be summarized as following:
a) OHV: 100-120 mg KOH per gram sample,
b) AV: 0.3-1.0 mg KOH per gram sample, c) IV: 5-15 g I$_2$ per 100 g sample,
d) moisture content: 0.04%,
e) OOC: 0.08%,
f) viscosity: 3000-3600 cP at 25° C.

EXAMPLE 7

The procedure in example 1 was repeated using a blend of RBD palm olein and SBO (95:5) where 2850 g of RBD palm olein was blended with 150 g of SBO in a 10 liters vessel. For the epoxidation reaction, the required amount of hydrogen peroxide (50%) was 324.5 g and formic acid (94%) was 1199.2 g. The product was worked-up in the usual manner described in example 1. The yield of epoxidized oil obtained was about 88%. The moisture content after drying is 0.048% and OOC is 3.38%.

EXAMPLE 8

About 2820 g of the dried epoxidized oils from example 7 was subjected to alcoholysis reaction with ethylene glycol and boron trifluoride complex as described in example 2. The required amount of ethylene glycol and boron trifluoride are 353.0 g and 12.5 ml respectively. The product was worked-up in the manner described in example 2 to give the yield of the desired product about 90-95%.
Properties of the polyol can be summarized as following:
a) OHV: 110-130 mg KOH per gram sample,
b) AV: 0.3-1.0 mg KOH per gram sample,
c) IV: 5-15 g I$_2$ per 100 g sample,
d) moisture content: 0.04%,
e) OOC: 0.02%,
f) viscosity: 7000-7500 cP at 25° C.

The present disclosure includes as contained in the appended claims, as well as that of the foregoing description. Although this invention has been described in its preferred form with a degree of particularity, it is understood that the present disclosure of the preferred form has been made only by way of example and that numerous changes in the details of construction and the combination and arrangements of parts may be resorted to without departing from the scope of the invention.

The invention claimed is:

1. A process to purify epoxidized oil produced from a reaction between per-acid and unsaturated oil, comprising the steps of:
   (a) washing the epoxidized oil with salt water upon separating the epoxidized oil from an aqueous fraction of any spent acids;
   (b) neutralizing an acidic condition of the washed epoxidized oil with a base; and
   (c) removing any base residue by washing the neutralized epoxidized oil with the salt water until the pH of the neutralized epoxidized oil is 6.5 to 7.5 to acquire the purified epoxidized oil, wherein the concentration of the salt in the salt water is 4% to 30% to avoid emulsion forming in the washing step, wherein the salt is selected from the group consisting of potassium chloride, sodium chloride, lithium chloride, and combinations thereof.

2. The process according to claim 1, wherein the per-acid is selected from the group consisting of peroxyformic acid, peroxyacetic acid, trifluoroperoxyacetic acid, benzyloxyperoxyformic acid, 3,5-dinitroperoxybenzoic acid, m-chloroperoxybenzoic acid, and combinations thereof.

3. The process according to claim 1, wherein the unsaturated oil is selected from the group consisting of palm oil, soybean oil, coconut oil, groundnut oil, safflower oil, linseed oil, corn oil, sunflower oil, olive oil, canola oil, cottonseed oil, rapeseed oil, tung oil, fish oil, lard, tallow, any derivatives thereof, and combinations thereof.

4. The process according to claim 1, wherein the base is selected from the group consisting of ammonia, metal carbonates, metal bicarbonates, anionic ion-exchange resin, and combinations thereof.

5. A process for producing oleochemical polyols, comprising the steps of:
   (a) epoxidizing unsaturated oil using an organic acid together with oxygenated water or a per-acid to obtain epoxidized oil;
   (b) washing the epoxidized oil with salt water to remove any unused organic acid together with the oxygenated water or the per-acid upon separating the epoxidized oil from an aqueous fraction of any spent acids;
   (c) neutralizing an acidic condition of the washed epoxidized oil with a base;
   (d) washing the neutralized epoxidized oil with the salt water until the pH of the neutralized epoxidized oil is 6.5 to 7.5 to remove any base residue;
   (e) reacting the washed neutralized epoxidized oil with polyhydric alcohols in the presence of boron trifluoride-diethylether complex to produce the oleochemical polyols, wherein the concentration of the salt in the salt water is 4% to 30% to avoid emulsion forming in the washing step, wherein the salt is selected from the group consisting of potassium chloride, sodium chloride, lithium chloride, and combinations thereof.

6. The process according to claim 5, further comprising the step of drying the washed neutralized epoxidized oil to achieve a moisture content below 1% before reacting with polyhydric alcohols.

7. The process according to claim 5, further comprising the steps of:
   (f) washing the produced oleochemical polyols with salt water;
   (g) neutralizing an acidic condition of the washed oleochemical polyols with a base;
   (h) washing the neutralized oleochemical polyols with the salt water until the pH of the neutralized oleochemical polyols is 6.5 to 7.5 to remove any base residue; and
   (i) drying the washed neutralized oleochemicals polyols to achieve a moisture content below 1%, wherein the concentration of the salt in the salt water is 4% to 30%, wherein the salt is selected from the group consisting of potassium chloride, sodium chloride, lithium chloride, and combinations thereof.

8. The process according to claim 5, wherein the epoxidizing step is performed at a temperature of 35° C. to 65° C.

9. The process according to claim 5, wherein the step of reacting the washed neutralized epoxidized oil with polyhydric alcohol in the presence of boron trifluoride-diethylether complex is performed at a temperature of 60° C. to 100° C.

10. The process according to claim 5, wherein the unsaturated oil is selected from the group consisting of palm oil, soybean oil, coconut oil, groundnut oil, safflower oil, linseed oil, corn oil, sunflower oil, olive oil, canola oil, cottonseed oil, rapeseed oil, tung oil, fish oil, lard, tallow, any derivatives thereof, and combinations thereof.

11. The process according to claim 5, wherein the organic acid is selected from the group consisting of formic acid, acetic acid, trifluoroacetic acid, benzyloxy formic acid, 3,4-dinitrobenzoic acid m-chlorobenzoic acid, and combination thereof.

12. The process according to claim 5, wherein the per-acid is selected from the group consisting of peroxyformic acid, peroxyacetic acid, trifluoroperoxyacetic acid, benzyloxyperoxyformic acid, 3,5-dinitroperoxybenzoic acid, m-chloroperoxybenzoic acid, and combinations thereof.

13. A process according to claim 5, wherein the base is selected from the group consisting of ammonia, metal carbonates, metal bicarbonates, anionic ion-exchange resin, and combinations thereof.

14. The process according to claim 5, wherein the base is prepared in a solution with a concentration that ranges from 1% to 20% by weight.

15. The process according to claim 5, wherein the polyhydric alcohols are selected from the group consisting of glycerol, pentaerythritol, ethylene glycol, propylene glycol, trimethylolpropane, sorbitol, xylitol, sucrose, D-glucose, fructose, and combinations thereof.

16. The process according to 5, wherein the boron trifluoride-diethylether complex has a concentration of 0.1 to 10% by weight of total reactant.

* * * * *